(12) United States Patent
McCann et al.

(10) Patent No.: US 9,926,591 B2
(45) Date of Patent: *Mar. 27, 2018

(54) FLUID IDENTIFICATION SYSTEM AND PRODUCTION AND USE THEREOF

(71) Applicant: Tracesa Ltd., Winchfield, Hook Hampshire (GB)

(72) Inventors: Dominic Patrick Joseph McCann, Winchfield (GB); Kevin John Forbes, Winchfield (GB); Edyta Lam, Preston (GB); Geoffrey Colin Maitland, Whittlesford (GB); Alexander Bismarck, Peterborough (GB)

(73) Assignee: Tracesa, Ltd., Winchfield (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/044,886

(22) Filed: Feb. 16, 2016

(65) Prior Publication Data

US 2016/0160269 A1    Jun. 9, 2016

Related U.S. Application Data

(63) Continuation of application No. 14/099,828, filed as application No. PCT/EP2012/056230 on Apr. 4, 2012, now Pat. No. 9,322,056.

(30) Foreign Application Priority Data

Apr. 5, 2011  (GB) .................................... 1105761.9

(51) Int. Cl.
| | |
|---|---|
| *E21B 49/00* | (2006.01) |
| *C12Q 1/68* | (2018.01) |
| *E21B 43/26* | (2006.01) |
| *C09K 8/80* | (2006.01) |
| *C40B 30/02* | (2006.01) |
| *G01N 33/28* | (2006.01) |

(52) U.S. Cl.
CPC ............ *C12Q 1/6813* (2013.01); *C09K 8/805* (2013.01); *C12Q 1/68* (2013.01); *C12Q 1/686* (2013.01); *C40B 30/02* (2013.01); *E21B 43/26* (2013.01); *G01N 33/2882* (2013.01)

(58) Field of Classification Search
CPC ...... C12Q 1/68; C07H 21/04; G01N 33/2882; E21B 43/26; E21B 47/1015
See application file for complete search history.

(56) References Cited

U.S. PATENT DOCUMENTS

| | | | |
|---|---|---|---|
| 5,665,538 | A | 9/1997 | Slater et al. |
| 8,053,744 | B2 | 11/2011 | Bortolin |
| 8,596,354 | B2 | 12/2013 | Hartshorne et al. |
| 9,322,056 | B2 | 4/2016 | McCann et al. |
| 2003/0027336 | A1 | 2/2003 | Maitra et al. |
| 2006/0088861 | A1 | 4/2006 | Higuchi et al. |
| 2010/0258743 | A1 | 10/2010 | Bortolin |
| 2014/0220563 | A1 | 8/2014 | McCann et al. |

FOREIGN PATENT DOCUMENTS

| | | |
|---|---|---|
| GB | 2439777 A | 1/2008 |
| WO | WO 90/14441 A1 | 11/1990 |
| WO | WO 91/17265 A1 | 11/1991 |
| WO | WO 98/56363 A1 | 12/1998 |
| WO | WO 01/81914 A1 | 11/2001 |
| WO | WO 2007/148058 A2 | 12/2007 |
| WO | WO 2010/140032 A2 | 12/2010 |
| WO | WO 2012/136734 | 10/2012 |

OTHER PUBLICATIONS

European Search Report, EP 15 17 1945, dated Oct. 2, 2015.
Third Party Observations for UK Patent Application No. GB1206061.2, dated Aug. 8, 2013.
Examination Report Under Section 18(3), UK Patent Application No. GB1206061.2, dated Aug. 29, 2014.
Examination Report under Section 18(3) from GB1105761.9, dated Jun. 6, 2013.
Examination Report under Section 18(3) from GB1105761.9, dated Mar. 1, 2013.
Examination Report under Section 18(3) from GB1105761.9, dated Oct. 17, 2012.
Zelikin, A., et al., "Disulfide-Stabilized Poly (Methacrylic Acid) Capsules: Formulation, Cross-Linking, and Degradation Behavior," Chemistry of Materials, vol. 20, pp. 2655-2661, 2008.
Zelikin, A., et al., "A General Approach for DNA Encapsulation in Degradable Polymer Microcapsules," ACS Nano, vol. 1 (1), pp. 63-69, (2007).
Tsarevsky, N. V. and Matyjaszewski, K., "Combining Atom Transfer Radical Polymerization and Disulfide/Thiol Redox Chemistry: A Route to Well-Defined (Bio) Degradable Polymeric Materials," Macromolecules, 38, 3087-3092, (2005).
Tsarevsky, N. V. and Matyjaszewski, K., "Reversible Redox Cleavage/Coupling of Polystyrene with Disulfide or Thiol Groups Prepared by Atom Transfer Radical Polymerization," Macromolecules, 35, 9009-9014, (2002).
Nicolay, R., et al., "Synthesis of Multisegmented Degradable Polymers by Atom Transfer Radical Cross-Coupling," Macromolecules, 40, 9217-9223, (2007).
Parker, A. J. and Kharasch, N., "The Scission of the Sulfur-Sulfur Bond," Chemical Reviews, 583-628, (Mar. 20, 1959).

(Continued)

*Primary Examiner* — Narayan Bhat
(74) *Attorney, Agent, or Firm* — Hamilton, Brook, Smith & Reynolds, P.C.

(57) ABSTRACT

A fluid identification system comprising a plurality of particles, each particle encapsulating therein at least one tracer material having an identifiable DNA, the at least one tracer material being encapsulated by an encapsulation material, wherein the particles are adapted to retain the at least one tracer material in an encapsulated form after exposure of the particles to a temperature of at least 75° C. and/or a pressure of at least 1000 psi ($6.9 \times 10^6$ N/m$^2$).

22 Claims, 7 Drawing Sheets

(56) References Cited

OTHER PUBLICATIONS

Rikkou, M. D. and Patrickios, C. S., "Polymers Prepared Using Cleavable Initiators: Synthesis, Characterization and Degradation," Progress in Polymer Science, 36, 1079-1097, (2011).

Katsikasi, L., et al., "The Thermal Stability of Poly(methyl methacrylate) Prepared by RAFT Polymerisation," J. Serb. Chem. Soc, 73 (8-9), 915-921, (2008).

Daraboina, N. and Madras, G., "Thermal and Photocatalytic Degradation of Poly(methyl methacrylate), Poly(butyl methacrylate), and Their Copolymers," Ind. Eng. Chem. Res., 47, 6828-6834, (2008).

Guaita, M., "Thermal Degradation of Polystyrene," British Polymer Journal, vol. 18, No. 4, 226-230, (1986).

Cleland, W. W., "Dithiothreitol, a New Protective Reagent for SH Groups," Biochemistry, vol. 3, No. 4, 480-482, (Apr. 1964).

Margosch, D., et al., "High-Pressure-Mediated Survival of Clostridium botulinum and Bacillus amyloliquefaciens Endospores at High Temperature," Applied and Environmental Microbiology, 72(5):3476-3481, (May 2006).

Feng, et al., "Intraceullular Uptake and Release ofPoly(ethyleneimine)-co-poly(methyl methacrylate) Nanoparticle/pDNA Complexes for Gene Delivery," International Journal of Pharmaceutics, 311(1-2):209-214, (Mar. 2006).

International Search Report and The Written Opinion of the International Searching Authority from PCT/EP2012/056230, dated Jun. 19, 2012.

Combined Search and Examination Report under Sections 17 and 18(3) from GB1105761.9, dated Jul. 29, 2011.

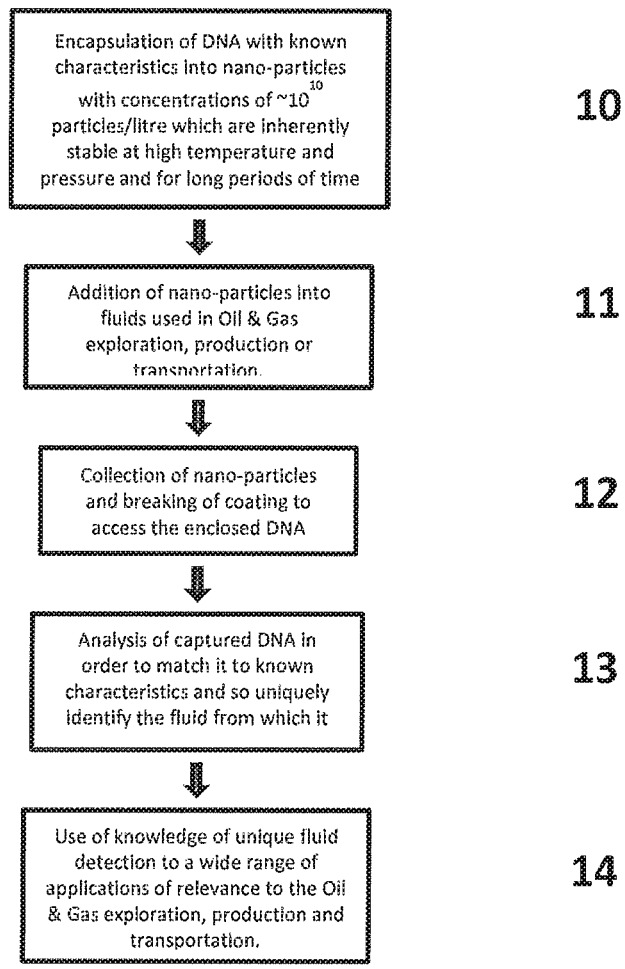
Figure 1. Generalised Workflow

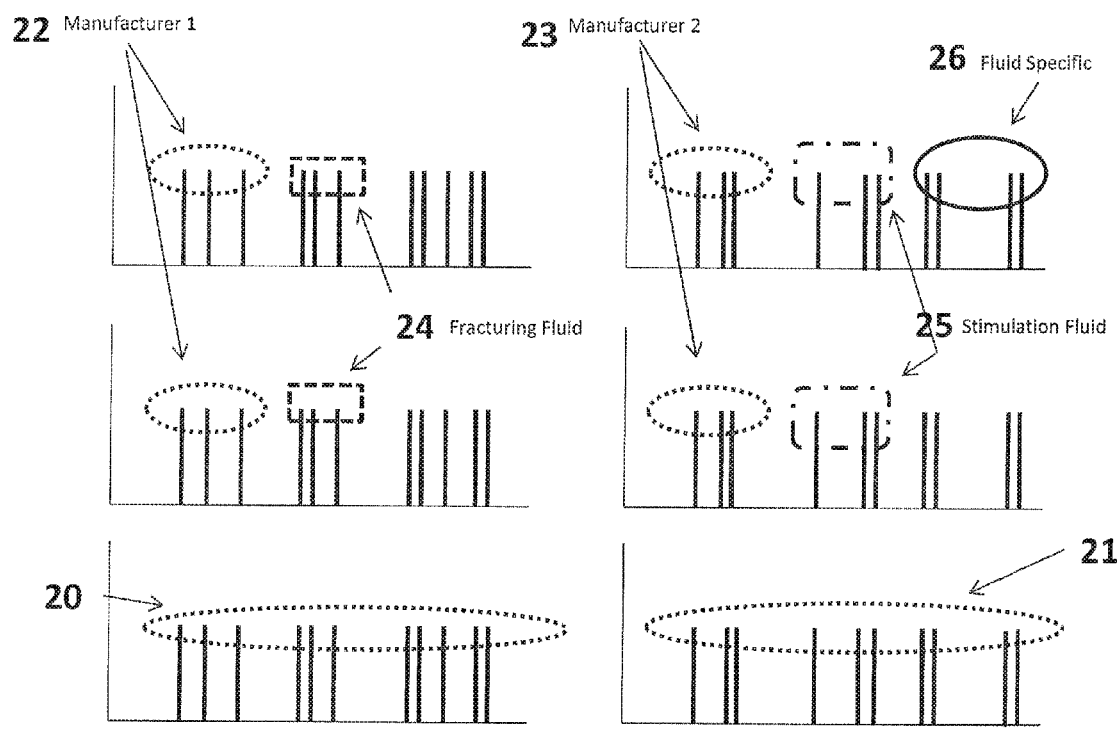
Figure 2. Example of Identification Schema

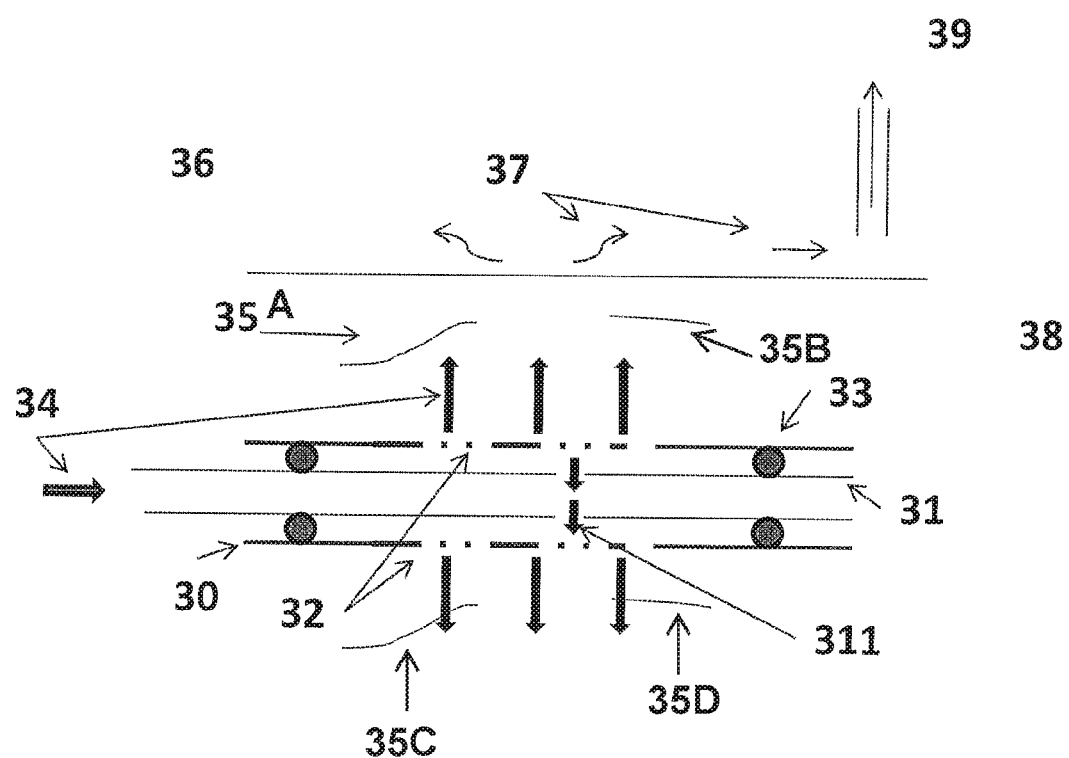
Figure 3. Illustration of flow of fracture fluid

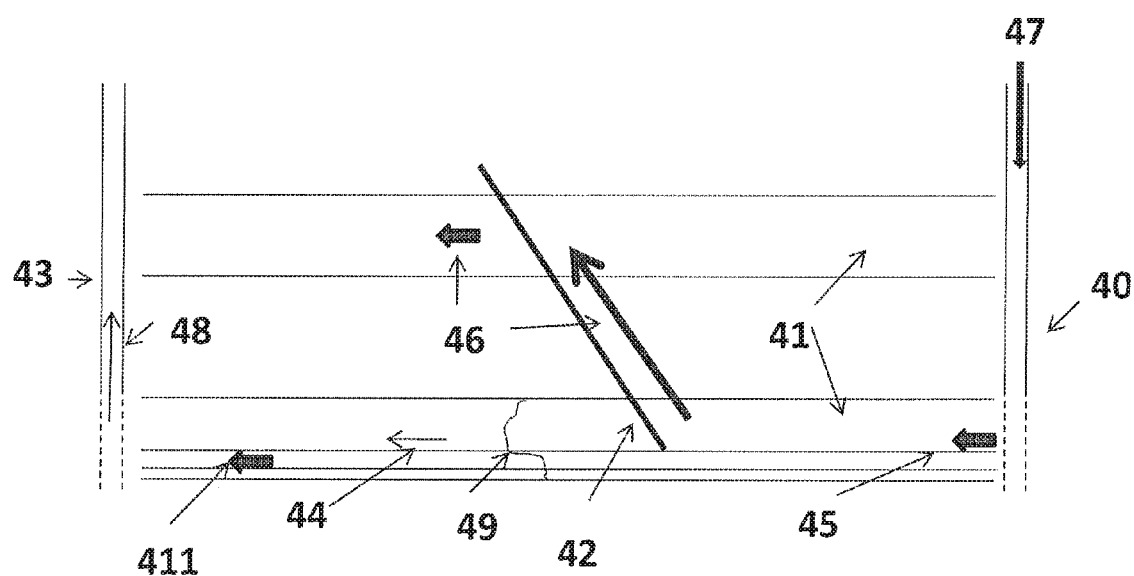
Figure 4. Illustration of EOR Cross-flow

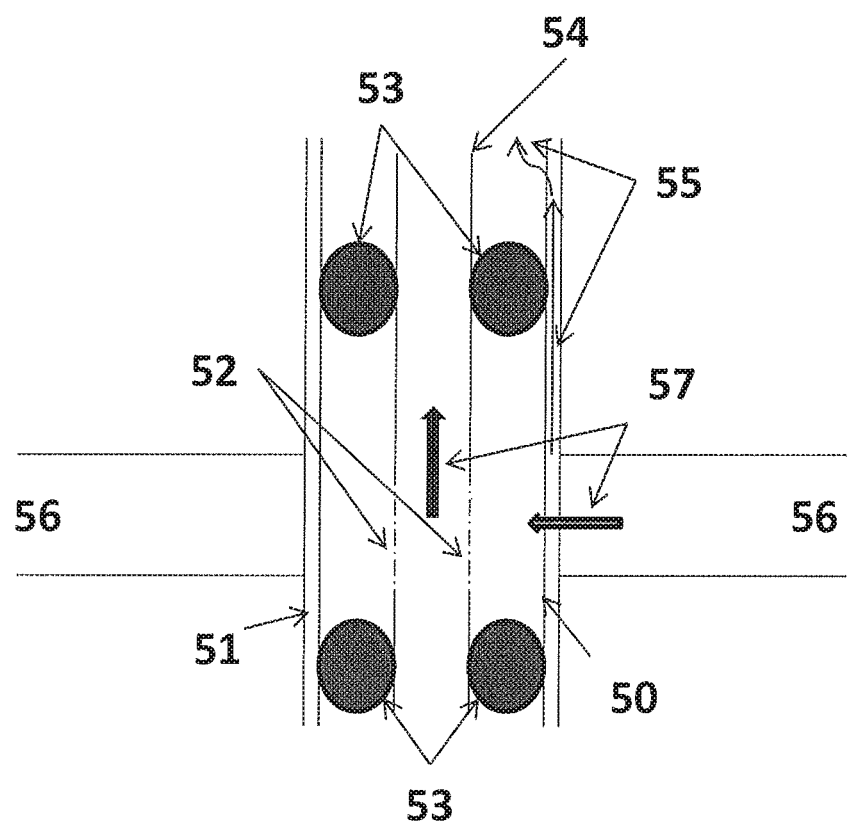
Figure 5. Illustration of Behind Casing Leak Path

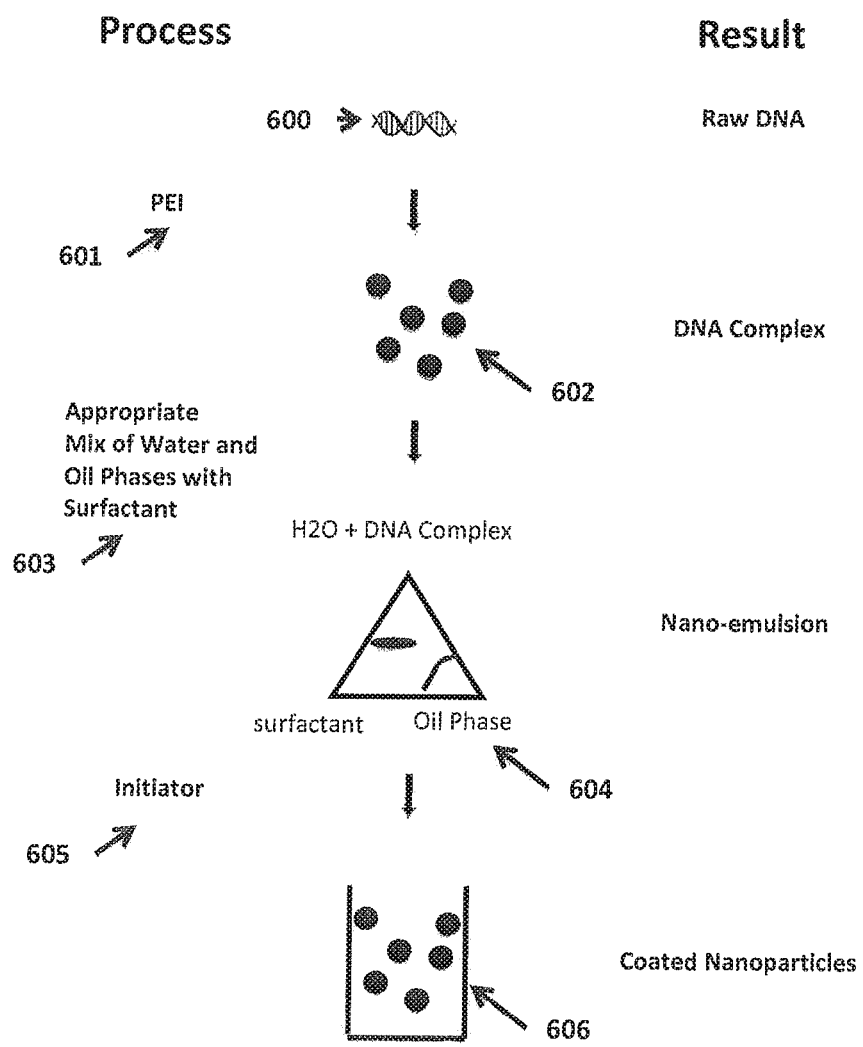
Figure 6A. Nanoparticle Manufacture process

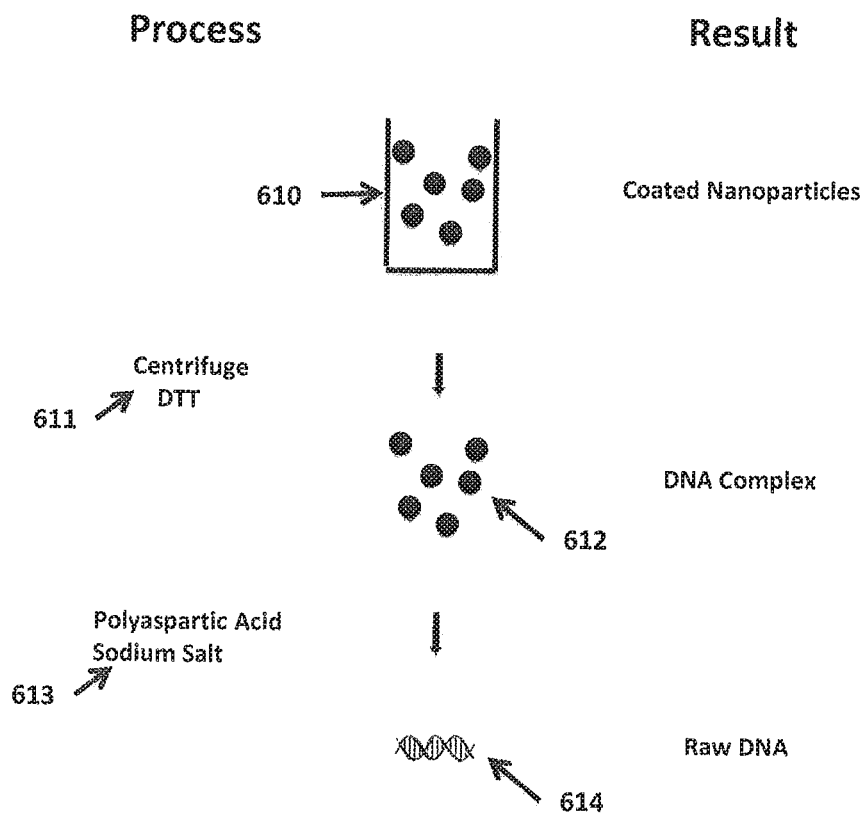
Figure 6B. Nanoparticle Disassociation process

FLUID IDENTIFICATION SYSTEM AND PRODUCTION AND USE THEREOF

RELATED APPLICATIONS

This application is a continuation of U.S. application Ser. No. 14/009,928, which is the U.S. National Stage of International Application No. PCT/EP2012/056230, filed on Apr. 4, 2012, published in English. This application claims priority under 35 U.S.C. §119 or 365 to Great Britain Application No. 1105761.9, filed Apr. 5, 2011. The entire teachings of the above applications are incorporated herein by reference.

The present invention relates to a fluid identification system, a method of producing a fluid identification system and a method of identifying a fluid. In particular, this invention relates to a tracer technology and the applications thereof within the oil and gas exploration, production and transportation industries.

Many different fluids are introduced, produced or moved during the oil and gas operations of exploration, production and transportation. These fluids range from those manufactured to perform specific functions to those collected from different formations in a well. Some of the fluids collected are fluids originally injected into the well or reservoir rocks, returning to the surface during operations such as drilling mud or fracturing fluids. Other fluids which are used occur naturally in the formation rocks, for example, oil, gas condensate and water. Of course, in many cases fluids collected can be a mixture of naturally occurring fluids and fluids introduced in to reservoir rocks.

During the life of a well or oil field many different kinds of fluids are used and a lot will be returned during production. It is important to understand how the fluids that are injected move through the 'system' which consists both of the reservoir rocks and the wells that are drilled into the formation. The information gleaned from this understanding can tell the operator (for example, the oil company managing the field) a lot about the efficiency of production of oil and gas, how well certain specialized fluids are working, e.g., stimulation fluids, whether fluids are moving from one production zone to another (for example, through the reservoir rock or behinds seals in a well that are meant to isolate these zones) and also if some of the fluids injected are finding away into shallower aquifers which could lead to environmental issues.

In particular, there are growing concerns that recent significant fracturing operations in shale gas formations create fracture paths where fracturing or stimulation fluids or naturally occurring formation fluids/gases flow into nearby aquifers. Early identification or confirmation that such flow is not occurring would be of significant value to the operator and society in general. In addition a better understanding of these fluid flows can allow the operator to change or adjust the production strategies in order to improve the overall productivity of the field.

As an example, it is a common practice during the later production phases of a field to inject water (or other fluids or gases) into a reservoir formation through one or more wells in the field, in order to 'sweep' the remaining oil in the reservoir formation towards the producing wells. This is one technique of a range collectively called enhanced oil recovery (EOR) methods.

However, if a lot of the injected water is flowing through natural fractures or faults into a different reservoir formation then the efficiency of the 'sweep' can be much reduced. Understanding these issues early can allow the operator to change the EOR strategy (e.g., try to seal the fractures or switch injection into a different reservoir formation) in order to improve the field productivity. The ability to detect and understand these issues early has significant value for the operator.

However, it should be understood that during the life of a field, a significant number of different fluids are used and the system can be very complex since it involves the reservoir rocks, both naturally occurring and operation induced fractures, faults, and the collection of wells that are drilled through overlying rock formations into the reservoir rocks. Therefore the tracking of these fluids is very complex and requires technology not presently available today.

A common practice that is used today to try and understand fluid flow is to use what is called a tracer. In general the tracer is added to a fluid at one point in the process and is detected at another point later in the process. For example, it is common to add a tracer to the drilling mud and to detect it in the mud that returns to the surface. If the time the tracer is added and the time it is first detected in the returns are compared then the fluid circulation time can be easily calculated as the difference between the two. This circulation time can help establish if the well is being cleaned properly or if the holed drilled is in gauge or washed out.

There exist several tracer technologies used in the oil and gas business today. Generally they can be categorized into two types:

As nonreactive, easily differentiated material placed in the mud circulating system at a certain time to be identified when it returns to surface. Mud tracers are used to determine circulation time. Dyes, paints, glitter or any material that will follow the mud can be used.

A chemical or isotopic marker that is uniformly distributed in the continuous phase of a drilling, coring or completion fluid and used to later identify the filtrate in cores or in fluids sampled from the reservoir. The tracer must become part of the filtrate, remaining in solution and moving with the filtrate into permeable zones. It should not be absorbed on clays or degrade. It needs to be measurable in trace amounts and safe to handle. Examples include: Weakly emitting radioisotopes which can be safe and effective, Bromide or iodide compounds are practical because they do not occur naturally in most muds or reservoirs and Nitrate anion added as sodium, potassium or calcium nitrate is one of the earliest tracers but it is difficult to analyze and degradation can be significant.

The application of any of these methods is limited in that they generally provide a single tracer. That is, it can be difficult or impossible to tag multiple fluids and differentiate between them. Long term events such as detection of injected water from offset injection wells are very difficult due to degradation of the tracer with time. As a result, Mathematical modelling is still the primary method of estimating (quantifying) the flow of different fluids within the reservoir or between different reservoir horizons, for example, through fractures or faults etc. However, these models require many assumptions which results in a broad range of possible outcomes.

It is known to use raw DNA as a tracer. In fact, companies such as TraceTag (www.tracetag.com) already put this raw DNA into oil tankers and storage tanks so that a spill can be identified by extracting the DNA from spill samples and matching it to known characteristics. However, this only works in refined products as DNA is easily destroyed and any contact with water, for example, renders it useless as a tag. In addition, these solutions are not practical at high pressures and temperatures experienced in oil and gas reservoirs.

WO91/17265 A1 (SLATER) describes this methodology. It discloses the use of raw DNA for the application of tagging crude oil or other refined products at ambient (conditions found at the earth's surface) temperatures and pressures. There is also the discussion of placing the DNA in 'beads' which dissolve in oil in order to tag the said oil and in which the 'beads' must have a 'specific gravity' similar to the oil in order to prevent settlement. Such limitations are often impractical and cannot provide a solution for downhole applications where the temperatures and pressures very high.

The following discloses an invention which utilizes inherently stable nanoparticles which do not 'dissolve' and do not require a specific 'specific gravity' and can be deployed in high temperature and high pressure environments found in the subsurface of oil and gas operations.

WO01/81914 A1 (SINVENT) discloses the concept of adding trace elements, which are 'chemically immobilized/integrated in the formation or wellbore completion equipment'. The trace elements are released on exposure to certain fluids, e.g., oil or water, or on the trigger of a pre-defined event, e.g. a change in fluid pH to some threshold value. The method requires that the trace elements are chemically immobilized/integrated and therefore must be 'put in place' during the construction of the well to be released at some later time. This necessarily limits its application and requires the use of specific and potentially costly equipment in the well and the operational cost to deploy or 'put in place' the said immobilized trace elements. It also somewhat restricts the application to new wells.

Other methods of tagging materials at ambient conditions are disclosed. For example, WO90/14441 A1 (CETUS) discloses the idea of 'bonding' nucleic acids to materials, e.g. covalently bonding. However this requires the necessary processes to achieve this 'bonding'. In addition, maintaining these bonds at high temperatures and pressures is not possible using the invention as disclosed.

These issues represent a significant limitation to the use of DNA as a tracer in the oil and gas industry.

This invention addresses these complexities and the limitations of technology presently used.

The present inventors have worked to establish technical solutions to the above restrictions associated with the technology presently used in the industry or disclosed in the prior-art.

The present invention accordingly provides a fluid identification system comprising a plurality of particles, each particle encapsulating therein at least one tracer material having an identifiable DNA, the at least one tracer material being encapsulated by an encapsulation material, wherein the at least one tracer material is complexed with at least one first polymer surrounded by the encapsulation material which comprises at least one second polymer.

The present invention also provides a fluid identification system comprising a plurality of particles, each particle encapsulating therein at least one tracer material having an identifiable DNA, the at least one tracer material being encapsulated by an encapsulation material, wherein the particles are adapted to retain the at least one tracer material in an encapsulated form after exposure of the particles to a temperature of at least 75° C. and/or a pressure of at least 1000 psi (6.9×10$^6$ N/m$^2$).

The present invention further provides a method of producing a fluid identification system, the method comprising the steps of: a. providing at least one tracer material having an identifiable DNA; b. complexing the at least one tracer material with at least one first polymer in a solvent; and c. encapsulating the at least one tracer material complex in an encapsulation material comprising at least one second polymer to form a plurality of particles, each particle comprising encapsulation material surrounding the at least one tracer material complex.

The present invention further provides a method of producing a fluid identification system, the method comprising the steps of: a. providing at least one tracer material having an identifiable DNA; polymerizing a polymerizable material in a liquid to form a plurality of particles including polymerized material, each particle comprising polymerized material encapsulating therein the at least one tracer material.

The present invention further provides a method of identifying a fluid, the method including the step of: a. adding the fluid identification system according to the invention or produced according to the method of the invention to a fluid.

The present invention further provides a library of a plurality of fluid identification systems according to the invention or produced according to the method of the invention, each fluid identification system in the library having a unique DNA signature to provide uniquely identifiable particles.

The present invention further provides a catalogue of the library of the invention.

The present invention further provides a computer database system storing the catalogue of the invention.

Preferred features of the present invention are defined in the dependent claims.

The present invention is at least partly predicated on the finding by the present inventors that the development of a uniquely identifiable fluid code which can provide millions of codes would address a lot, if not all, of the issues which limit tracer uses today; that DNA can provide a unique identifier; and that a particle encapsulating the DNA can be produced which can protect the DNA against degradation as a result of being subjected to environmental conditions which are typically prevalent in hydrocarbon production units, such as oil and gas installations.

DNA is used extensively in forensic science and medical fields. Because of these widespread applications, technology is readily available that can be used to amplify and simultaneously quantify a targeted DNA molecule, for example, qPCR (quantitative polymerase chain reaction). It is readily available off the shelf technology and DNA matching can be performed automatically. Computer software techniques exist for this purpose. Although qPCR is the preferred technology used in this invention, clearly others which provide the similar functionality could also be used and so may be alternatively employed in this invention. It is also well known that DNA samples can be obtained with known, unique and predefined characteristics.

Preferred aspects of the invention relate to the manufacture, deployment, collection and analysis of nanoparticles which are distributed in the continuous phase of all fluids that are used within these oil and gas industries. The applications of these nanoparticles for the better understanding of reservoir fluid flow and also the movements of fluids within a well (e.g., from one formation to another or from one well section to another) or between wells (e.g., during injection operations) are some of the embodiments described in this invention. This includes the cataloging, traceability and management of oil field fluids.

The present invention discloses a unique technology to address the 'tracer' method of monitoring fluids during oil and gas exploration, production and transportation operations. The needs are quite broad and will be discussed later but some key ones are related to better understanding of fluid flow in a reservoir for production optimization (enhanced recovery techniques), cross-flow between wells or formations, identification of potential leak paths, monitoring of fracture and stimulation fluids and environmental monitoring. Including, cataloguing and indexing of fluids for identification and efficient management.

According to a first embodiment of this invention, there is provided a means to enclose the DNA material within a coating that protects the DNA against the environment commonly experiences in oil and gas reservoirs and wells. Preferably the coated or enclosed DNA is formed into nanoparticles which are inherently stable over a wide range of temperature, e.g. at least 75° C. and pressures, e.g., at least 1000 psi ($6.9 \times 10^6$ N/m²). Optionally, the particles are adapted to retain the at least one tracer material in an encapsulated form after exposure of the particles to a temperature of from 75 to 400° C. and/or a pressure of from 1000 to 35000 psi ($6.9 \times 10^6$ N/m² to $241.5 \times 10^6$ N/m²), further optionally a temperature of from 100 to 250° C. and/or a pressure of from 1000 to 15000 psi ($6.9 \times 10^6$ N/m² to $103.5 \times 10^6$ N/m²), still further optionally a pressure of from 5000 to 15000 psi ($34.5 \times 10^6$ N/m² to $103.5 \times 10^6$ N/m²).

The inherent stability allows the particles to exist for very long periods of time, e.g. for a period of at least six months, optionally from 6 months to 10 years, further optionally from 1 year to 5 years.

The particles, and the encapsulated DNA, are able to survive exposure to aqueous and hydrocarbon environments in such temperature and/or pressure regimes. Such environments may include a mechanical environment to which the fluid will be subjected, e.g., passing through pumps, nozzles, valves, flowing through torturous paths, pipeline, fractures in formation, pore throats in rock formations, etc. Also, the particle environments may comprise fluids that can contain solids, e.g. drilled cuttings or sand produced from the rock formation.

Although, encapsulation of DNA into particles has been achieved, see U.S. Pat. No. 6,555,376 as an example, these solutions have biodegradable coatings which have a very limited stability so that they cannot be used for the applications described in this invention. They are focused at delivering drugs or genetic material to cells within the human body and are designed to release these. Creating an inherently stable nanoparticle which can withstand the environment commonly found in the oil and gas industry has not been achieved in the prior art.

Preferably encapsulation is achieved by use of formulation of polymer-coated droplets by carrying out interfacial polymerization in emulsions. Preferably this takes place at ambient conditions, so avoiding exposure of the DNA to high temperatures during encapsulation, with the size varied from nanometers to microns by choosing either (nano) emulsions or suspensions at the starting point.

According to a second embodiment of this invention, there is provided a means to selectively release the DNA for within the particles so that it can be analyzed and matched to known characteristics. Preferably, by making multiple emulsions (e.g., oil-in-water-in-oil) and as necessary modifying the monomers so that it has both water-soluble and oil-soluble groups, the initial location of the DNA, monomer and polymerization initiator/cross-linker can be manipulated to enable polymerization to occur at the liquid-liquid interface to encapsulate the DNA, in order to control carefully the nature of the coating and how the DNA is released.

Preferably, the coating will be based on high melting acrylate-, methacrylate- or styrene-based polymers. Preferably, a disulphide cross-linker is used to increase the solvent and thermal resistance of the coating. Moreover, the cross-links can be reduced under relatively mild conditions by, for example, dithiothreitol (DTT) reagents, which provides a means for selectively degrading the coating of the particles and so releasing the DNA.

Preferably, a route to facilitate easy separation/concentration of the dilute DNA nanocapsules in the recovered liquid stream is to incorporate a magnetic nanoparticle core into the nanocapsules so that it can be captured using a magnetic separation stage.

Although a preferred embodiment for the creation of DNA encapsulated particles and the release of this DNA on recovery is described, it is also envisaged in this invention that other techniques to create nanoparticles which enclose the DNA may be possible.

According to a third embodiment of this invention, a manufacturing process, preferably based on the above embodiment, allows significant numbers of DNA capsules are produced, e.g., of order $10^6$, optionally $10^{10}$ particles/liter. The particles may have an external dimension of from 1 nanometer to 10 microns, optionally from 10 nanometers to 1 micron, further optionally from 50 nanometers to 500 nanometers.

According to a fourth embodiment of this invention, volumes of fluids containing the said DNA capsules (note that the use of the term nanocapsules and nanoparticles is used interchangeably) are added to fluids (or process fluid) which are pumped into a well, field or reservoir. Or into fluids which are collected during production and before transportation. Preferably, the quantity of DNA nanocapsules per volume of fluid pumped can be controlled in order to obtain a desired concentration per unit volume in the input or injection stream, for example 100 to 1000 particles per liter. In another embodiment of this invention, the DNA nanocapsules are added to fluids at the point of manufacture so that the fluids are appropriately tagged before delivery to the operations.

According to a fifth embodiment of this invention, DNA capsules can be manufactured which enclosed DNA characteristics with a significant number of uniquely identifiable capsules, e.g., >1,000, unique tags. Preferably, DNA capsules with specific characteristics will be used as part of a structured schema. As an example, a manufacturer of different fluids can be assigned capsules with specific DNA base characteristics and the fluids provided by this manufacture have additional characteristics in addition to the base characteristics which uniquely define the fluid itself. This is akin to members of a family having the same DNA sequences (note DNA characteristics, signature and sequences are used interchangeably within this invention) identifying them as part of a family but with other sequences that are unique to them as individuals.

In yet another embodiment, grouping of DNA sequences can be applied to specific types of fluids, e.g., all fracture fluids would have common base sequences which identify them as fracturing fluids and stimulation fluids would have different base characteristics which identify them as stimulation fluids etc. These can be in addition to sequences which identify them as having been manufactured by a specific manufacturer and other DNA signatures which uniquely identify the fluid itself. A sequence may also identify the owner, for example the organization accountable for the fluid during its life cycle, e.g. cradle-to-grave responsibility, for example the operator, oil company or service company).

Preferably, industry wide catalogues of manufacturers and fluids can be produced allocating specific DNA sequences to manufacturers and fluid types. Preferably such a catalogue is captured in a computer database and appropriate search algorithms. While this describes a preferred embodiment of this invention, it is understood that there can be many different characterization schema employing the unique features of the DNA nanocapsules or nanoparticles described in this invention. These other schemas are within the scope of this invention.

According to a sixth embodiment of this invention, fluids that are retrieved from an Oil and Gas reservoir or from a well used to produce fluids or inject fluids into such a reservoir, or fluids retrieved by taking samples of reservoir fluids using methods such as are used by the use of 'logging' tools run on wireline, coiled tubing or other forms of tool conveyance, are analyzed in order to capture DNA capsules that may be entrained within the said retrieved fluids.

According to a seventh embodiment of this invention, fluids or materials retrieved from rock samples or drilled cuttings or other formation rocks are analyzed in order to capture the DNA nanoparticles that may be contained within the said fluids or materials. Examples include fluids which are contained within 'core' samples which are commonly retrieve from a well using practices well known to the industry. Mud cake which is often present on the surface or which has penetrated into these cores (sometimes call filtrate) can represent a material which can contain DNA capsules which were previously injected into reservoir, either through the same well from which the core is retrieved or through other wells in the oil and gas field.

According to an eighth embodiment of this invention, captured DNA nanocapsules or particles are selectively treated to break the coating of the said particles in order to release the DNA enclosed. Preferably the breaking of the coating is as described in other embodiments of this invention. Preferably the released DNA is analyzed using qPCR techniques which can amplify and simultaneously quantify a targeted DNA molecule. Matching of DNA characteristics to known catalogues of DNA sequences (as described in another embodiment of this invention) can identify information about the origin of the DNA capsule and so the fluid in which it was originally added to. This can include but is not limited to; the manufacture of the fluid, the type of fluid and the specific fluids itself.

According to a ninth embodiment of this invention, a system is provided which allows the manufacture of DNA capsules or particles of known characteristics, whereby these capsules are added to any or all fluids which are used or produced during oil and gas exploration, production and transportation activities, and whereby fluids or materials collected during said operations are treated to capture the added DNA capsules. In addition, the captured DNA capsules are treated in order to release the enclosed DNA for analysis whereby unique fluids identification is achieved.

According to a tenth embodiment of this invention, a fluid identification system as described in other embodiments of this invention is used to calibrate reservoir modelling software and processes in order to provide the operator with a better understanding of fluid flow within the reservoir. As an example, a common method of providing enhanced oil recovery (EOR) is to inject water (or other fluids/gases) into a formation through an offset injection well. This has the effect of pushing or sweeping the oil present in this formation towards other wells through which it is produced.

However, if there exist communication paths (e.g., natural faults or factures) which cause the injected water to by-pass the formation it was intended to flood or which cause the water to be channelled through formations in which there is no oil or where small amounts of oil are swept (e.g. high permeability stringers), then the efficiency of the EOR process can be greatly compromised.

By entraining the DNA nanocapsules as described in other embodiments of this invention and detecting these specific capsules or particles at different points in the reservoir (by taking samples or other commonly used techniques) the flow path of the injected water can be mapped. In addition, by noting the times of injection and the times of detection, it is possible to establish the transit time of the injection water within the formation. This is very valuable information that can be used to calibrate reservoir models and thus significantly improve their predictive capabilities. The calibration may also be of a fluid flow system, such as a circulation time in a well, or a well/formation combination, or a well/completion equipment/formation combination. The DNA signature can time-stamp the usage of the fluid. The DNA signature can identify the well, reservoir or zone in a reservoir where the fluid has been used, and/or the treatment type into which it has been introduced. The DNA signature can provide an initial timestamp for when the fluid is first introduced into the system, e.g., pumped into the well, pumped into a reservoir zone or pumped into a fracture. In addition to providing a time stamp for the fluid, a plurality of successive time stamps for the fluid may be provided, including an initial timestamp potentially coded in the DNA signature.

According to an eleventh embodiment of this invention the fluid identification system as described in other embodiments of this invention is used to detect leak paths within the well/formation system. As an example, it is common practice to cement a casing or tubing into the well that was drilled into the reservoir rocks. Additionally, several productive layers of reservoir rocks can exist and it is common to perforate the said casing at different locations adjacent to these productive layers so that oil from the layers can flow from the formation into the casing for collection. It is also common practice to isolate these perforation zones so that oil for different layers can be produced independently, also because the formation pressures in these layers can be different it is possible that oil will flow from one layer to the other through the well without coming to surface. This is not desirable. However, if the cement which is used to secure the casing in place is not of the correct mix or is put in place incorrectly, then there can exist leak paths behind the casing so that even if the perforation zones are correctly isolated within the casing, communication behind the casing can occur. It is desirable to know that this is occurring so that corrective measures can be taken.

By injecting the DNA capsules or particles described in this invention with known and uniquely different characteristics into the different perforation zones and by then detecting the presence of these capsules or particles in different zones will allow the detection of flow between these zones. In addition, if it is known that the formations do not communicate within the formation itself then the communication can be due to behind the casing leak paths.

According to a twelfth embodiment of this invention the fluid identification system as described in other embodiments of this invention is used to provide fluid transit times. In this case the DNA signature added to a fluid that is being pumped into a well or formation can be modified with time. As a result the time at which the fluid is pumped into the well or formation can be recorded. The time this particular DNA signature is identified in fluid that returns to the surface or in fluid samples extracted from a well or from the formation can also be noted so that the transit time of the said fluid can be computed as the difference between the two.

This feature has many applications. For example, fracture fluids that are first pumped into a fracture could be coded (or time stamped) with one unique DNA signature and fracture fluid pumped at a later time could be coded with a different unique DNA signature. In fact, it is possible to change the DNA signature of the nanoparticles added to this fluid on an hour by hour basis (or any time increment as needed). By identify these specific DNA signatures in the return fluids (or other fluids samples collect from a well or from the formation rocks) a transit or time-lapse profile can be created. As example, when the first fracture fluids pumped into a fracture is detected in the returns, the operator will be sure that the whole fracture has been cleaned out completely. The same method may be used for other natural or man-made flow paths. Such time-lapse information can also be used for monitoring fluid flow from one well, e.g., an injection well, through the reservoir to another well, e.g., a production well. This data is of significant value when used to calibrate reservoir models and so improve their predictive abilities.

Through these listed embodiments and aspects of this invention, the inventors have provided different embodiments which cover some of the potential applications of the unique fluid identification system described. However, it is understood that this is a subset of the potential applications and those skilled in the art will appreciate that there can be many others which are additionally envisaged in this invention.

BRIEF DESCRIPTION OF THE DRAWINGS

Embodiments of the present invention will now be described, by way of example only, with reference to the accompanying drawings, in which:

FIG. 1 is a generalized workflow in accordance with an embodiment of the present invention;

FIG. 2 schematically illustrates a number of exemplary DNA identification spectra in accordance with a second embodiment of the present invention;

FIG. 3 shows a schematic illustration of the detection of fracture or other fluid which is in accordance with yet another embodiment of this present invention;

FIG. 4 schematically shows the detection of cross-flow as part of an EOR methodology which is in accordance with another embodiment of the present invention;

FIG. 5 schematically illustrates the detection of behind casing flow which is in accordance with another embodiment of the present invention; and FIGS. 6A and 6B schematically illustrate, respectively, a nanoparticle manufacture process and a nanoparticle disassociation process in accordance with another embodiment of the present invention.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

Hereinafter, the present invention will now be described in more detail with reference to the accompanying FIGS. 1 to 6A-6B, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

Referring to FIG. 1 where a generalized workflow is shown that captures some of the embodiments of this invention. In a step 10, of the workflow, DNA with specific characteristics or signatures is encapsulated within nanoparticles which have the specific features that they are inherently stable at temperatures >100° C. and at pressures >5000 psi (>34.5×10$^6$ N/m$^2$) for long periods of time, typically >1 year. Encapsulation is achieved by use of formulation of polymer-coated droplets by carrying out interfacial polymerization in emulsions. This takes place at ambient conditions, so avoiding exposure of the DNA to high temperatures during encapsulation, with the size varied from nanometers to microns by choosing either (nano) emulsions or suspensions at the starting point. The coating is based on high melting methacrylate or styrene based polymers. A disulphide cross-linker is used to increase the solvent and thermal resistance of the coating. Moreover, the cross-links can be reduced under relatively mild conditions by e.g., dithiothreitol (DTT) reagents, which provides a means for selectively degrading the coating of the particles and so releasing the DNA. The release of the DNA is labelled as step 13 in the workflow in FIG. 1.

During oil and gas exploration, production and transportation operations many fluids are used or collected. Some of these fluids have special functions, for example, cleaning the wellbore to allow oil to easily flow. These fluids can be very expensive and in some cases quite dangerous to human health, e.g., acids. Therefore it is important to track them and ensure that they are used safely. In step 12 of the workflow, nanoparticles are added to these fluids. The DNA within the nanoparticles will contain a coding which allows each fluid to be uniquely identified.

The introduction of the nanoparticles into the fluids can occur at the well site as the fluids are pumped into the well or they can be added at the point of manufacture and so arrive at the well site already tagged with its unique identifier. Those skilled in the art will appreciated that adding these kinds of particles to the fluids can take place at many different places within the processes of exploration, production or transportation.

The particles will be added in very large quantities, e.g., on the order of 10$^{10}$ particles, which because of their very small size will become entrained within the fluid flow becoming part of the bulk volume. For example, they will not settle as perhaps grains of sand would. They follow the fluids where ever it flows and this includes into the reservoir rocks themselves. Again because of their nano-size they will easily pass through the pore throats and fractures within the reservoir without blocking or impeding flow. This is a very important feature of this invention. In step, 10, particles are manufactured such that concentrations of ~10$^{10}$ particles/liter are produced. Therefore, as many liters of fluid containing these particles can be added to process fluids as is required to provide the desired number of particles as needed to deal with, e.g., dilution as the process fluids flow through the system. Those skilled in the art will appreciate the volumes required depending on the fluids or operation that is being monitored.

It is also common practice for fluids to be collected during the various processes that occur during oil and gas exploration, production and transportation. These fluid samples can be collected at surface when fluids that are pumped into a well or wells returns to surface. Fluids can also be collected directly from the rock formations using specialist tools well known to the industry call logging or production logging tools. These instruments are lowered into the well and can 'draw' fluids from the rocks into fluid-chambers in the tool itself. The captured fluids are pulled back to surfaced in the tool and the fluids can be sent to laboratories (either on the well site or elsewhere) in the fluid-chamber where it can be analyzed chemically and/or physically. It is also known that rock core samples can be obtained by use of specialist tools or during drilling/coring operations. These cores are brought to surface for analysis and again the fluids within the core or the material such as 'mud filtrate' can be accessed at surface using standard procedures.

In the workflow of FIG. 1, in step 12 nanoparticles are collected from any fluids retrieved and broken to release the DNA enclosed and in step 13 the DNA is matched to known fluid signatures as described later. In one embodiment of this invention, magnetic nanoparticles are encapsulated with the DNA in order to facilitate the collection of particles using a magnetic field.

Those skilled in the art will appreciate that while $\sim 10^{10}$ particles can be added to process fluids, modern techniques such as qPCR can make a reliable detection of specific DNA molecule sequences with use of material from just $\sim 100$-1000 particles. Therefore significant dilution is possible without loss of functionality. It should also be appreciated that a collected fluid sample can contain DNA particles from different source fluids. It is a feature of this invention that the relative number or ratio of DNA particles attributed to one process fluid compared to another can be used to estimate the concentration of the different fluids within the sample.

Referring to FIG. 2, six graphs are shown. It should be noted that the information on the graphs is purely illustrative in nature and they show the presence of specific DNA sequences as vertical lines or indications at specific points on the horizontal axis. It is appreciated by those skilled in the art that there can be many graphical or other ways to illustrate the presence or otherwise of specific DNA sequences in a sample, e.g., graduated colored bar-graphs etc.

In FIG. 2 is illustrated just one way which has been chosen in order to facilitate the explanation of embodiments of this invention. Each vertical line can be consider to illustrate the presence of a sequence and all the lines taken together can be used to illustrate the presence of a specific DNA signature. These plots will be used for explanatory purposes solely and, in fact, those skilled in the art will appreciate that such sequences and signatures may not even been seen as DNA matching can be performed in an automated fashion.

Returning to FIG. 2, reference numeral 20 shows a DNA signature which is unique. In this invention, the DNA is encapsulated as described in other embodiments within nanoparticles and introduced into a process fluid to uniquely identify it. Samples collected and which contain this DNA signature show that the source process fluid which was tagged with this unique DNA signature is present in the sample and without any doubt. In FIG. 2, reference numeral 21 shows a DNA signature of a second fluid which also has its own unique signature so that the two source fluids which have signatures 20 and 21 can be uniquely identified.

Therefore, it is an embodiment of this invention that any process fluid can be laced with DNA capsules which have signatures which are unique so that these process fluids can be individually identified during any operation in oil and gas exploration, production or transportation. Those skilled in the art will appreciate the value of such a feature and will see that there are numerous applications which are envisaged in this invention.

It is also appreciated that a DNA signature can be broken down into constituent sequences which can be used for further refinement of an identification schema. As an example, parts of the signature can be used to uniquely identify a manufacturer of a particular fluid as illustrated by reference numerals 22 and 23 in FIG. 2 where the pattern shown in reference numeral 22 identified one particular manufacturer and reference numeral 23 identifies a second manufacturer.

In one embodiment all manufactures of fluids will have their own specific pattern which uniquely identifies them. In addition, it is also possible to use another part of the signature to identify a particular type of process fluid. In FIG. 2, the element of the signature labelled 24 could be used to distinguish the fluid as a fracture fluid (as an example) and a different pattern as labelled 25 would identify the fluid as a stimulation fluid. In this illustration, the last part of the signature 26 would identify the specific formulation of the fracturing or stimulation fluids.

An industry wide catalogue of manufactures, fluid types and specific formulations can be developed. In some ways this is akin to members of a family having specific features of their DNA which identify them as a family member and other features which identify them as unique individuals.

Those skilled in the art will appreciate that what is described in FIG. 2 is a limited set of examples which clearly defines the concept captured in this invention and that many different embodiments of this concept are possible. These other embodiments are within the scope of this invention. Another example could be to 'group' fluids that are pumped into a specific reservoir rock (or layer) with its own unique part of the signature. In this case, if one of these process fluids is detected in some other part of the reservoir then it must have arrived there through the rock formations or through leak paths in the well system. Some of these examples will be described with the aid of FIGS. 3-5 below.

FIG. 3 shows a simplified schematic of the flow of fracturing fluid in a horizontal well that has been drilled into a formation 38 which could be, for example, gas shale. Gas shales are particular reservoir rocks which have very low permeability such that gas does not flow through them very well. In order to produce gas from them it is generally necessary to 'fracture' the shale so that flow-paths are created for the gas to flow back into the well. In this example, a casing 30 is cemented into place and has been perforated with perforations 32 at some specific locations. Inner tubing 31 has been run inside the casing 30. A means to communicate 311, (e.g., a valve, not shown) fluids from inside the tubing 31 to outside the tubing 31, and vice versa, are provided. Also a means to isolate the particular zone of the casing 30 around the perforations 32 is provided using packers 33.

High pressure fracturing fluids 34 are pumped from surface down the tubing 31, through the valve 311, through the perforations 32 and into the formation 38. Because the formation rocks are of very low permeability and due to the very high hydraulic forces produced, the formation rocks fracture to create a network of fracture paths, 35A, 35B, 35C, 35D. These operations can require the pumping of significant volumes of fracture fluids, typically on the order of 100s of barrels per minute, and over long periods of time (many days). Proppants can be pumped into the fracture network to ensure they remain open for gas flow. The objective is to create a large fracture network 35A, 35B, 35C, 35D from which the gas can flow back to tubing 31 and to surface once the fracturing operation is complete and the well is put onto production. These operations are well known to those skilled in the art and can take many forms.

However, if during these operations the fracture network extends to an overlying permeable formation 36 as shown in FIG. 3, then leak paths 37 can be created and fracture fluid can flow thought the permeable zone. It is possible that an offset well 39, which could be a water well if the overlying permeable zone is an aquifer, can become contaminated. The illustration in FIG. 3 is quite simplistic but those skilled in the art can appreciate that the leak path(s) can be across many overlying/underlying formation rocks through natural fractures or faults in the rock.

In an embodiment of this invention, samples collected from offset wells or from the same well at different depths and nanoparticles captured as described in other embodiments, can be analyzed to determine the DNA signatures so as to determine if fracture fluids or any other type of processing fluid used during any operation, is present. The samples can be collected by any one of many methods that are common to the industry.

FIG. 4 shows yet another embodiment of this invention. This figure shows a schematic of an enhanced oil recovery (EOR) technique involving the injection of water into a reservoir rock in order to sweep oil towards a production well 43. In FIG. 4 there are two permeable layers of reservoir rocks 41. The lower layer 41 has oil present but its pressure is no longer sufficiently high enough to allow oil to flow 48 naturally to surface through the production well 43. An offset well 40, which could have started its life as a production well, is used to inject water down from surface 47 into the lower permeable layer. The water 45 enters into the layer and pushes the oil towards the production well 43. An interface 49 can be created whereby water exists to the right hand side and oil exists to the left hand side as shown in FIG. 4. However, if a fault or fracture 42 exists then a large portion of the injected water 45 can traverse the fault 42 up into the top permeable layer 41 along path 46. This results in a much smaller portion of the injected water flow 45 being available to push oil towards the production well 43. This is illustrated by the smaller arrow 44. In this is scenario the efficiency of the EOR process is much reduced and another method may need to be deployed.

Other scenarios could result in the injected water being channelled through a thin highly permeable lay in the lower reservoir rock 411, by-passing the oil in the layer and so resulting in very low sweep efficiency. However, technology available today makes it very difficult to detect these kinds of issues with any degree of accuracy.

One embodiment of the present invention uses the nanoparticles which contain a unique DNA signature to be injected with the injection water 47. If it is detected very early (early in this context could be months instead of years) in the production stream from 43 then it can be an indication of a high permeable zone by-passing the sweep. Or if it is detected in samples taken from the upper reservoir layers then it is an indication of cross-flow between layers. This information is of significant value to an operator of the field as EOR techniques can be modified or changed in order to optimize production from the field.

FIG. 4 shows some simplified examples, however, those skilled in the art will appreciate that there can be many other scenarios in which a unique fluids identification system as described in other embodiments of this invention can be used to detect and thus be used to optimize reservoir production.

FIG. 5 shows yet another embodiment of this invention which illustrates the identification of behind-casing flow. FIG. 5 shows casing 50 which has been cemented in place and is therefore enclosed in cement 51 which fills the gap between the wellbore wall and the outer surface of the casing 50. This cement 51 holds the casing 50 in place but also provides a seal so that reservoir fluids cannot flow up the annulus between the casing 50 and the wellbore. In FIG. 5, there exists a producing formation layer 56 from which oil is produced. An inner tubing 54, comprising production tubing, has a means, such as ports 52, to allow oil to flow from the casing 50 into the tubing 54. The oil flows from the reservoir layer 56, through perforations (not shown) in the casing 50 and through the communication ports 52, into the tubing 54 and up to surface for collection. The flow path is labelled 57. The annular zone between the casing 50 and the production tubing 54 is isolated by mean of the packers 53 shown in FIG. 5.

However, what is illustrated in FIG. 5 is that the cement 51 has not been put in place correctly or its formulation is not correct for the environment in which it is being used. As a result, a leak path or channel has developed which links the perforation zone with areas in the well above the packers 53. The path is illustrated by 55. This can be a dangerous situation as hydrocarbons now have a potential path up the well other than through the controlled path generated by the production tubing 54. Such an issue would require immediate remediation. However, it can be very difficult to identify such a leak path early as it could be very small and initially the flow through it can be difficult to identify.

In one embodiment of this invention, nanoparticles containing known and unique DNA signatures are pumped into the producing reservoir rocks, e.g., entrained in the fracturing or stimulation fluids. They can also be pumped and entrained in the cement 51 itself. Samples taken from the annulus between the casing 50 and tubing 54, in areas above or below the specific zone isolated by packers 53, are then analyzed so as to detect the presences of these unique DNA signatures. The detection of these unique signatures is an indication of cross-flow behind the casing 50 or potentially behind the packers 53. It is well known in the industry that packers 53 can be replaced or inflated to higher pressures in order to create the required sealing. If, however, the cross flow continues then it is likely it is occurring behind the casing 50 and a more involved remedial process is urgently required.

EXAMPLE

In the following section we provide a worked example. It is understood that what follows consists of process steps which might be performed in a different order than presented. It is also anticipated that those skilled in the art could substitute certain steps for others and/or omitted or modify certain steps and/or substitute certain materials for others which are similar in nature or that provide a similar functionality or result to those here described. The disclosed invention is therefore in no way limited by the details of the provided working example shown.

FIGS. 6A and 6B provide workflows or process flows to manufacture and disassociate the micro/nanoparticles previously described, respectively.

In FIG. 6A the process starts with biological tagging material such as raw DNA. This can be naturally occurring DNA material with a known signature or preferably synthetic or manufactured DNA of known characteristics or signature. The signature may have specific characteristics in order to follow a particular identification schema, examples of which are illustrated in FIG. 2. This DNA is labelled 600 in FIG. 6A.

A first preferred step is to create a physical protection of the DNA. For example one method uses cationic or hydrogen bonding polymers. This provides additional protection to the DNA during the process steps that follow. This step is labelled 601 in FIG. 6A and the resulting DNA complexes are labelled 603.

DNA complexes are prepared by mixing specific concentrations of encapsulating polymer and DNA in a suitable buffer. For example TE buffer is a commonly used buffer solution used in molecular biology especially involving DNA, used to solubilize DNA while protecting it from degradation. The mixture is left to equilibrate at room temperature for some specific time period. One example uses polyethylene imine (PEI) an encapsulating polymer, with the amounts of PEI and DNA selected so that the PEI nitrogen to DNA phosphorus ratio is between 1 and 60. Preferably a PEI nitrogen to DNA phosphorus ratio of between 5 and 30 is used. A particular working example uses a PEI nitrogen to DNA phosphorus ratio of 20. However other ratios could be employed in this invention.

Also, other polyelectrolytes could be utilized as the encapsulating polymer, for example, poly-L-Lysine or hydrogen bonding polymers such as polyethylene glycol. In this worked example PEI has been selected.

The minimum equilibration time is preferably between 1 and 120 minutes, more preferably between 5 and 60 minutes. However, greater or shorter times could be employed. The process is labelled 601 in FIG. 6A and the resulting DNA complexes are shown as 602 in the same FIG.

It has been shown experimentally using methods for DNA detection known to those skilled in the art, for example, gel chromatography, UV spectroscopy, or fluorescence spectroscopy, that there is no degradation of the DNA within the complex as result of the above processes or as a result of the processes that follow.

In FIG. 6A the next step in the workflow is to create a stable micro-emulsion of water phase droplets in the oil phase. Preferably this is a water-in-oil emulsion which is a thermodynamically stable micro-emulsion. Throughout the following example and through this invention, a nano-emulsion can substitute for a micro-emulsion depending on the size of the water phase droplets. The water phase contains the DNA complexes fabricated in the previous steps and described earlier. The amount of DNA complex can be varied to achieve a desired concentration of DNA in the final emulsion. Preferably a DNA concentration from 0.001 to 30 μg/ml is used, the upper limit being set by the gelation limit of the particular DNA being used. More preferably a DNA concentration from 0.1 to 5 μg/ml has been used. However, it is appreciated by those skilled in the art that any concentration up to the gelation point can be used. Here gelation is defined as the point at which the DNA complex solution becomes too viscous to spontaneously form an emulsion or to form an emulsion using methods known to those skilled in the art.

In order to achieve a stable micro-emulsion, there are 3 or more components that need to be mixed in the correct ratios. These are; surfactant(s), an oil phase which may subsequently be polymerized or cross-linked and the DNA/water phase.

Suitable surfactants are typically non-ionic amphiphilic molecules. Preferably they are polyethylene oxide (PEO)-polypropylene oxide (PPO) copolymers or PEO-hydroxyalkyl ester triblock copolymers. More preferably, surfactants such as sorbitan alkanoates or polyalkene anhydrides can be used. In addition blends of these and other surfactants with other co-surfactants, such as alkanols, sorbitan esters or alkanoic acids, can be used. However, in this invention many other types of surfactants with similar characteristics or which provide the same results could be utilized such as alkylpolyethers, alkyl alkylene oxide block copolymers or alkyl-alkylene diols. In the specific example described here, the water phase consists of polyethylene imine/DNA complex (with an N:P ratio of 20 and DNA concentration 1 μg/ml) in TE buffer.

The oil phase comprises, or optionally consists of, polymerizable monomers or co-monomers, optionally diluted by a suitable solvent. The solvent may be, for example, selected from alkanes, alkanols, or ketones, and is chosen such that it is a solvent for the monomers/comonomers but not for the resulting polymer. The monomers are selected to be capable to form an outer solid protective coating for the aqueous droplets containing the DNA complexes, created by interfacial polymerization at the water phase/oil phase interface in the micro- or nano-emulsion.

Monomers and co-monomers can be used which lead to any polymer which is hydrolytically stable under the temperature, pressure, pH and other relevant conditions of the application. For oil well and oil reservoir applications, the choice may be restricted to monomers which can be polymerized by free radical polymerization processes, such as styrene, methyl methacrylate, or vinylpyrrolidone. The polymerization initiator may be contained in either the oil phase or the water phase, preferably the water phase. For other applications, such as groundwater tracers, polyurethanes, epoxy polymers or similar polycondensation polymers may be suitable.

An alternative procedure for all applications is for the oil phase to comprise, or consist of, a solution of a polymer or mixture of polymers containing chemical groups which can be cross-linked to form a cross-linked polymer layer at the oil phase/aqueous phase interface. This process can be augmented or complemented by using polymer solutions which have a lower critical solution temperature (LCST) or upper critical solution temperature (UCST) which enables the polymer to precipitate from the solution by an increase or decrease in temperature respectively.

It is also preferable that chemically-breakable (by, for example, chemical reduction or hydrolysis) chemical linkages are also incorporated into the polymer chains. Possible groups include esters, urethanes, carbonates, disulphides or amines. Suitable linkages are groups which are stable under the application conditions (such as under the temperatures, pressures, pH and salinities typically found in oil and gas wells or reservoirs) but which can subsequently be preferentially broken by the application of a suitable chemical or physical trigger e.g. a chemical breaker, a change in pH, temperature or pressure, the exposure to light or radiation or to an electrical or magnetic field, or to mechanical stirring.

More preferably disulphide (S—S) bonds are incorporated into the polymer chains, which can be broken at some later stage by a suitable reducing agent so that the polymer layer of the capsule is readily broken on demand. In the worked example, S—S bonds are used; however those skilled in the art may consider using other bonds or means to allow the polymer skin of the capsule to be broken. The described example uses polymethylmethacrylate (hereinafter MMA) as the preferred polymer because it has very high temperature and mechanical stability characteristics. In addition, its formation by polymerization can incorporate disulphide bonds. However, other polymers could be deployed, for example, polystyrene, that provides equally suitable properties for use in this invention.

In the worked example the oil phase can consist of purely MMA. However, in some instances it is advantageous for the oil phase to comprise MMA plus a hydrocarbon or other suitable diluent. The example provided has used pure MMA and also MMA plus hexane up to 99% by weight of the oil phase. The use of 80% by weight hexane as a diluent for the polymer, such as MMA has been found to be particularly suitable. However, in accordance with the invention other hydrocarbons or diluents can be utilized and the ratio of MMA to diluent can be varied in order to provide the desired concentration of monomer in the mixture.

In accordance with the invention, different surfactants may be used, depending on the amount of MMA used or the type of diluent. For example, it has been found that when MMA was used purely as the oil phase a sorbitan alkanoate surfactant in hexanol was efficient in forming a stable micro- or nano-emulsion. Polyethylene oxide di-1,2-hydroxyoctyl decanoic acid triblock copolymer can also be used. However, when both MMA and hexane were used in the oil phase, a blend of polyisobutylene succinic anhydride and sorbitan ester (surfactant S) gave stable and polymerizable micro-emulsions.

It will be readily understood by those skilled in the art that there exists a significant number of commercially available surfactants and diluents that can be utilized in accordance with various embodiments of this invention.

The selection and mixing of the appropriate surfactant, water phase and oil phase is illustrated by the process labelled 603 in FIG. 6A.

In this example, it is preferable to mix the three components in the ratios 5-30 w/w % surfactant(s): 40-80 w/w % oil phase: 10-55 w/w % water phase, more preferably 8.3 w/w % surfactant(s): 66.7 w/w % oil phase: 25 w/w % water phase.

However, it will be appreciated by those skilled in the art that varying ratios can provide a stable emulsion with differing properties, for example, greater amounts of DNA complex or 'thicker' layers of polymer after the interfacial polymerization has taken place during the next steps to be described later. For example, if a mix of sorbitan alkanoate/hexanol:MMA (oil phase):water phase is used then a stable emulsion is formed with the ratios 23.6 w/w % sorbitan alkanoate/hexanol: 74.2 w/w % MMA: 2.2 w/w % water phase.

The resultant stable micro-emulsion is labelled 604 in FIG. 6A.

The final step in the workflow used to fabricate micro/nanoparticles, as illustrated in FIG. 6A, is the addition of an initiator to trigger the interfacial polymerization process. This is labelled 605 in FIG. 6A.

There are many methods to achieve such polymerization in which breakable linkages are introduced into the polymer. Examples include but are not limited to: synthesis of copolymers of N,N-bis(acryloyl) cystamine (BAC) and MMA/styrene, synthesis of copolymers of allyl disulphide and MMA/styrene with V50 azo initiator and synthesis of copolymers of L-cystine and MMA/styrene. However in this example synthesis of MMA via micro-emulsion ATRP (Atom Transfer Radical Polymerization) has been chosen. It is understood that those skilled in the art may select another polymerization methodology to provide the same result and these other methods may be employed in alternative embodiments of this invention.

The synthesis of polymethyl methacrylate (MMA) via this route was chosen because ATRP is one method to introduce disulphide bonds (linkages) into the polymer. The polymerization occurs via formation of a radical on Bis[2-(2'-bromoisobutyryloxy)ethyl]disulphide (on the carbon atom adjacent to Br in the compound as shown below) and since Br resides on each end of the compound, initiation occurs from both ends of the molecule. The formation of polymer is by itself an evidence of introduction of disulphide linkages since an ATRP initiation can occur only by formation of a radical on bromide and not at disulphide linkages.

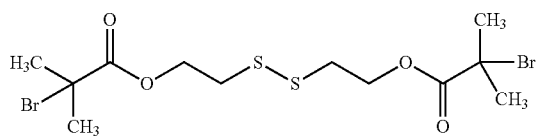 [SMILES: CC(C)(Br)C(=O)OCCSSCCOC(=O)C(C)(C)Br]

Therefore polymerization of micro-emulsions was carried out in this example using ATRP. Copper bromide, bi-pyridyl (Bpy) and bis[2-(2'-bromoisobutyryloxy)ethyl]disulphide were used as the initiator system, labelled 605 in FIG. 6A. Copper bromide and bi-pyridyl were used to form copper complex and bis[2-(2'-bromoisobutyryloxy)ethyl]disulphide was used to introduce S—S degradable links into the polymer.

The above describes an example workflow for the fabrication of nano- or micro-particles which incorporate DNA. However, this invention is in no way limited by the example provided and those skilled in the art may devise other workflows using the same or different materials to create nano- or micro-particles and these other workflows are within the scope of, and alternative embodiments of, this invention.

The process detailed in FIG. 6A can fabricate DNA nanoparticles which are numerous and can manufacture as many $10^{15}$ capsules per liter. They are inherently stable and can survive for very long periods of time, for example many years, in the environments found in oil and gas reservoirs. These nano- or micro-capsules or nano- or micro-particles can be deployed as described in other sections of this specification and as shown in the step labelled 11 in FIG. 1. Deployment can be into any oil and gas fluids systems used during the operations of exploration, production and/or transportation. They can contain DNA that has specific pre-defined signatures as illustrated in FIG. 2. The nano/microcapsules can be designed for and used in other fluid flow/tracer applications such as groundwater tracing, leak detection from agricultural wastes or landfills or industrial processes, and any general purpose fluid tagging applications where a resulting fluid is uniquely identifiable.

After introduction into a fluid system and after passing through that fluid system entrained in the fluid, the particles/capsules can be collected by any of the means described in other sections of this specification. Once fluid samples have been collected, the process of particle disassociation as shown in FIG. 6B is carried out. The objective is to release the DNA in order that it can be used for further analysis as described previously and thus providing a fluid identification and characterization of the fluid system under investigation. It should be noted that during the sampling process any background DNA can be destroyed before the particles are disassociated therefore ensuring that the only DNA present in the sample after disassociation is the DNA that was contained within the micro/nano particles.

FIG. 6B provides an example workflow or process, however, it will be understood by those skilled in the art that it is within the scope of this invention to modify this workflow or the materials used therein in order to achieve the same result. What is described in no way limits the disclosed invention to this particular example.

The starting point in the workflow is labelled 610 in FIG. 6B and represents a sample of fluid taken from the fluid system by any of the methods previously described or used in the industry. The sample can contain a certain number of nanoparticles (or microparticles) or capsules. The number will depend on many factors.

It is firstly required to collect or isolate these capsules from within the sample and remove the outer polymer coating. In this example, the coating consists of MMA incorporating disulphide bonds as described in the workflow or process illustrated in FIG. 6A and described above. One method to separate these capsules is to centrifuge the fluid sample. This is a method well understood by those skilled in the art. If magnetic material has been added to the capsules as described in other sections of this specification, then the application of a magnetic field can aid in this separation. However, there are other techniques that can be used to achieve this separation, for example, filtration or the presence of a specifically coated collection plate to which the particle are naturally attracted (for example, the attraction could be chemical or electrostatic) and all are within the scope of this invention. In this example, the addition of the reducing agent D,L-dithreitol (DTT) is used to break the disulphide bonds or links thus removing the MMA polymer layer and so releasing the DNA complexes as shown 612 in FIG. 6B. The step of centrifuging and the addition of DTT is labelled 611 in the same FIG. In addition, because the DNA is protected prior to this step, any background DNA existing in the sample can be denaturalized before adding DTT so that the only DNA that exists is that which is released during the particle disassociation steps here described.

The next step in the workflow or process releases the raw DNA from within the DNA complexes as labelled 613 in FIG. 6B. This must be achieved without damaging or denaturing the DNA. Preferably the steps labelled 611 and 613 in FIG. 6B are carried out at room temperature. In this example, polyaspartic acid sodium salt is used to release the DNA from within the complex. It has been shown using techniques known to those skilled in the art, for example, fluorescence spectroscopy or gel electophoresis, that naked DNA survivability is achieved through all steps described in FIGS. 6A and 6B.

The workflow illustrated in FIG. 6B represents a worked example of the step labelled 12 in FIG. 1. It has also been shown experimentally that the nanoparticles fabricated as shown in FIG. 6A survive the environmental conditions that they are anticipated to experience when passing through fluid systems used during the oil and gas operations of exploration, production and transportation, including those where the fluids pass through an oil and gas reservoir.

Once the raw DNA has been retrieved as outlined above, the DNA signature itself can be analyzed by off-the-shelf technology (not described herein) in order to identify signatures or characteristics in the raw DNA and to perform automated (or other) matching that in turn provides a fluids identification system as described in other sections of this specification.

For example, the matching can be performed against a known database of unique signatures providing details of, for example, the manufacturer of the fluid, the type of fluid, where the fluid was introduced into the process fluid system, how long the fluid has taken to pass through the system etc. The fluid system can be any type of fluid system used during the oil and gas operations of exploration, production and/or transportation as described in other sections of this specification.

Additionally the resulting better understanding of the said fluids system greatly enhances the ability of those skilled in the art to better manage the said oil and gas operations of exploration, production and transportation and therefore increase the value to the operator or owner or other stakeholders of the oil and gas reservoir and better manage the potential environmental impact of those operations as described previously.

In this detailed description several embodiments of this invention are described. They provide a detailed description of the concepts captured in this invention. However, it is by no means exhaustive and those skilled in the art will appreciate that other embodiments are possible which use the concepts described. These other potential embodiments cannot all be described but are however encompassed within the scope of this invention.

What is claimed is:

1. A method of identifying a fluid, the method including the step of:
(a) adding a fluid identification system to a fluid, the fluid identification system comprising a plurality of particles, each particle encapsulating therein at least one tracer material having an identifiable DNA, the at least one tracer material being encapsulated by an encapsulation material, wherein the encapsulated DNA has known and unique characteristics to provide a unique identifier for the particles, wherein the encapsulated DNA has, within the said characteristics, a first characteristic of a DNA signature which uniquely identifies a time parameter of a specific fluid into which the fluid identification system or a liquid containing the fluid identification system is added, wherein in adding step (a) the DNA signature and the time parameter of the addition provide a time stamp for the fluid, wherein the particles are adapted to retain the at least one tracer material in an encapsulated form after exposure of the particles to a temperature of at least 75° C. and/or a pressure of at least 1000 psi ($6.9 \times 10^6$ N/m$^2$);
(b) pumping the fluid into a well, field or reservoir of a hydrocarbon production unit, or a reservoir zone or fracture zone;
(c) retrieving the fluid identification system from a sample of the fluid;
(d) separating the at least one tracer material from the particles; and
(e) analyzing the identifiable DNA to determine the identity of the DNA and the time parameter of the fluid between adding step (a) and retrieving step (c).

2. A method according to claim 1 wherein in adding step (a) the first characteristic of the DNA signature of the identifiable DNA is recorded together with the time parameter of the addition to provide the time stamp.

3. A method according to claim 1 wherein a plurality of successive time stamps for the fluid is provided.

4. A method according to claim 3 wherein each time stamp includes the time parameter encoded into the DNA signature of the encapsulated DNA.

5. A method according to claim 3 wherein the plurality of successive time stamps is provided as the fluid is pumped into the well, field or reservoir of the hydrocarbon production unit, or the reservoir zone or fracture zone.

6. A method according to claim 5 wherein a fracture fluid is time stamped at multiple times and information established with respect to time of arrival of successive fracture fluid slugs is used to control a fracture clean out process.

7. A method according to claim 1 wherein the encapsulated DNA has a second characteristic of the DNA signature which uniquely identifies a usage location of the specific fluid into which the fluid identification system or a liquid containing the fluid identification system and in adding step (a) the DNA signature and the usage location of the addition provide a location stamp for the fluid.

8. A method according to claim 7 wherein in adding step (a) the second characteristic of the DNA signature of the identifiable DNA is recorded together with a usage location of the addition to provide the location stamp for the fluid.

9. A method according to claim 1 further comprising the step (f) of determining at least one parameter of at least one of a fluid transit path, a fluid transit time and a fluid transit time profile of fluid between adding step (a) and retrieving step (c).

10. A method according to claim 9 wherein the at least one parameter determined in step (f) is employed in a step (g) of calibrating a model of a hydrocarbon reservoir, or a fluid flow system.

11. A method according to claim 9 wherein the at least one parameter determined in step (f) is employed in a step (h) of calculating the efficiency of an enhanced oil recovery (EOR) method to recover trapped oil of a hydrocarbon reservoir.

12. A method according to claim 11 wherein the enhanced oil recovery (EOR) method comprises water injection into the hydrocarbon reservoir.

13. A method according to claim 9 wherein the at least one parameter determined in step (f) is employed in a step (i) of detecting at least one leak path in a rock formation or within a well completion system.

14. A method according to claim 13 wherein the at least one leak path comprises at least one of a fault and a fracture in the rock formation, or a natural or man-made flow path.

15. A method according to claim 13 wherein the at least one leak path is behind a casing or around a sealing element in a well completion system.

16. A method according to claim 9 wherein the at least one parameter determined in step (f) is employed in a step (j) of detecting actual or potential contamination of aquifers by fracture, stimulation or other process fluids.

17. A method according to claim 1 wherein the fluid includes a first fracture fluid which is pumped into a particular fracture zone and has a unique first DNA signature, and a second fracture fluid which is pumped into a different fracture zone and has a different unique second DNA signature, and in step (e) the analyzing step identifies the first and second DNA signatures to identify from which fracture zone the first and second fracture fluids have been retrieved.

18. A method according to claim 1 wherein the encapsulated DNA has at least one further characteristic or a plurality of further characteristics selected from: a third characteristic of the DNA signature which uniquely identifies the origin, manufacturer or owner of the fluid identification system or a liquid containing the fluid identification system; a fourth characteristic of the DNA signature which uniquely identifies a type of process fluid into which the fluid identification system or a liquid containing the fluid identification system is added; and a fifth characteristic of the DNA signature which uniquely identifies the specific fluid into which the fluid identification system or a liquid containing the fluid identification system is added.

19. A method according to claim 1 wherein in the well, field or reservoir of a hydrocarbon production unit, or the reservoir zone or fracture zone, the particles are exposed to a temperature of at least 75° C. and/or a pressure of at least 1000 psi ($6.9 \times 10^6$ N/m$^2$).

20. A method according to claim 1 wherein step (e) includes determining the identity of the DNA by employing a library of a plurality of fluid identification systems, each fluid identification system in the library having a unique DNA signature to provide uniquely identifiable particles.

21. A method according to claim 20 wherein the library has a catalogue which identifies, for each fluid identification system therein, a manufacturer and/or owner, fluid type, specific formulation and at least one DNA characteristic associated with each unique DNA signature.

22. A method according to claim 21 wherein in step (e) a computer database system is employed which stores the catalogue and the computer database system is programmed with at least one search algorithm to match an input DNA signature to signatures in the catalogue.

* * * * *

UNITED STATES PATENT AND TRADEMARK OFFICE
CERTIFICATE OF CORRECTION

PATENT NO. : 9,926,591 B2
APPLICATION NO. : 15/044886
DATED : March 27, 2018
INVENTOR(S) : Dominic Patrick Joseph McCann et al.

It is certified that error appears in the above-identified patent and that said Letters Patent is hereby corrected as shown below:

On the Title Page

Under item (63) Related U.S. Application Data:
Please delete: "Continuation of application No. 14/099,828"
And insert: --Continuation of application No. 14/009,928--

Signed and Sealed this
Fifth Day of June, 2018

Andrei Iancu
*Director of the United States Patent and Trademark Office*